(12) United States Patent
Karime

(10) Patent No.: US 10,385,280 B2
(45) Date of Patent: Aug. 20, 2019

(54) MINIMIZING COKE FORMATION IN A REACTOR STRIPPER

(71) Applicant: SABIC Global Technologies B.V., Bergen op Zoom (NL)

(72) Inventor: Mustapha N. Karime, Riyadh (SA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days.

(21) Appl. No.: 15/553,797

(22) PCT Filed: Feb. 23, 2016

(86) PCT No.: PCT/US2016/019074
§ 371 (c)(1),
(2) Date: Aug. 25, 2017

(87) PCT Pub. No.: WO2016/137955
PCT Pub. Date: Sep. 1, 2016

(65) Prior Publication Data
US 2018/0066195 A1    Mar. 8, 2018

Related U.S. Application Data

(60) Provisional application No. 62/121,883, filed on Feb. 27, 2015.

(51) Int. Cl.
*B01J 8/00* (2006.01)
*B01J 8/18* (2006.01)
(Continued)

(52) U.S. Cl.
CPC ............ *C10G 11/182* (2013.01); *B01J 8/003* (2013.01); *B01J 8/0025* (2013.01); *B01J 8/0055* (2013.01);
(Continued)

(58) Field of Classification Search
CPC . B01J 8/00; B01J 8/0015; B01J 8/0025; B01J 8/003; B01J 8/005; B01J 8/0055;
(Continued)

(56) References Cited

U.S. PATENT DOCUMENTS 2,994,659 A   8/1961   Slyngstad et al.
3,243,265 A   3/1966   Annesser
(Continued)

FOREIGN PATENT DOCUMENTS

GB        817127 A    7/1959

OTHER PUBLICATIONS

International Search Report for International Application No. PCT/US2016/019074; dated May 23, 2016; 5 pages.
(Continued)

*Primary Examiner* — Natasha E Young
(74) *Attorney, Agent, or Firm* — Cantor Colburn LLP

(57) ABSTRACT

The presently disclosed subject matter relates to systems and methods for catalyst regeneration. In particular, the presently disclosed subject matter provides for an integrated fluidized bed reactor and catalyst regeneration system to minimize hydrocarbon accumulation. In one embodiment, the presently disclosed subject matter provides for a fluidized bed reactor unit including a catalyst riser having a partially perforated surface in close proximity to a reactor stripper.

8 Claims, 2 Drawing Sheets

(51) Int. Cl.
*B01J 8/26* (2006.01)
*B01J 8/38* (2006.01)
*C10G 11/18* (2006.01)
*C07C 5/333* (2006.01)

(52) U.S. Cl.
CPC .......... *B01J 8/1863* (2013.01); *B01J 8/1872* (2013.01); *B01J 8/26* (2013.01); *B01J 8/388* (2013.01); *C07C 5/333* (2013.01); *C10G 11/18* (2013.01); *B01J 2208/0007* (2013.01); *B01J 2208/00061* (2013.01); *B01J 2208/00539* (2013.01); *B01J 2208/00575* (2013.01); *B01J 2208/00592* (2013.01); *B01J 2208/00628* (2013.01); *B01J 2208/00707* (2013.01); *Y02P 20/584* (2015.11)

(58) Field of Classification Search
CPC . B01J 8/18; B01J 8/1845; B01J 8/1863; B01J 8/1872; B01J 8/24; B01J 8/26; B01J 8/38; B01J 8/384; B01J 8/388; B01J 2208/00–00044; B01J 2208/00061; B01J 2208/0007; B01J 2208/00539; B01J 2208/00575; B01J 2208/00592; B01J 2208/00628; B01J 2208/00654; B01J 2208/00707; C07C 5/00; C07C 5/32; C07C 5/327; C07C 5/333; C10G 11/00; C10G 11/14; C10G 11/18; C10G 11/182
See application file for complete search history.

(56) References Cited

U.S. PATENT DOCUMENTS

| | | | | |
|---|---|---|---|---|
| 3,894,936 | A | * | 7/1975 | Owen ........................ B01J 8/24 208/120.01 |
| 4,135,886 | A | | 1/1979 | Kuchar |
| 4,167,553 | A | | 9/1979 | Persico et al. |
| 4,571,326 | A | | 2/1986 | Bischoff et al. |
| 4,727,216 | A | | 2/1988 | Miller |
| 4,766,266 | A | | 8/1988 | Khoobiar |
| 5,154,818 | A | * | 10/1992 | Harandi .................. C10G 11/18 208/113 |
| 5,370,789 | A | * | 12/1994 | Milne ...................... C10G 9/32 208/126 |
| 5,593,935 | A | | 1/1997 | Golunski et al. |
| 5,665,130 | A | * | 9/1997 | Nielsen ................... B01D 45/12 208/161 |
| 6,248,298 | B1 | | 6/2001 | Senior et al. |
| 6,569,389 | B1 | | 5/2003 | Koves et al. |
| 7,744,746 | B2 | | 6/2010 | Cunningham et al. |
| 2011/0114468 | A1 | | 5/2011 | Davuluri et al. |

OTHER PUBLICATIONS

Written Opinion of the International Search Report for International Application No. PCT/US2016/019074; dated May 23, 2016; 6 pages.

* cited by examiner

MINIMIZING COKE FORMATION IN A REACTOR STRIPPER

CROSS REFERENCE TO RELATED APPLICATIONS

This application is a 371 of International Application No. PCT/US2016/019074, now WO 2016/137955, filed Feb. 23, 2016, which claims priority to U.S. Application No. 62/121,883, filed Feb. 27, 2015, both of which are incorporated herein by reference in their entirety.

TECHNICAL FIELD

The presently disclosed subject matter relates to systems and methods for catalyst regeneration.

BACKGROUND

Fluidized catalyst cracking and dehydrogenation of hydrocarbons are important processes in the refining and petrochemical industry, and are used to produce intermediates for generating other hydrocarbons, such as olefins. These processes involve continuously circulating a fluidized catalyst between a reactor and a catalyst regenerator. In an integrated reactor and catalyst regenerator system, deactivated catalyst can be continuously removed from the reactor and transported to and from the catalyst regenerator for regeneration without requiring the shutdown of the reactor to replenish the deactivated catalyst.

Problems in conventional integrated reactor and catalyst regenerator systems include the accumulation of hydrocarbon within the stripper of the fluidized bed reactor. Large differences in the temperatures of the reactor stripper and the catalyst riser of a fluidized bed reactor known in the art result in condensation of hydrocarbon on the surface of the catalyst riser within the reactor stripper. This hydrocarbon buildup causes decreases in internal pressure resulting in mandatory shutdown of the fluidized bed reactor and production loss.

Catalytic reactor and regeneration systems are known in the art. For example, U.S. Pat. Nos. 4,135,886 and 4,167,553 disclose multiple-stage stacked catalytic reactor systems to be used with catalyst regeneration chambers. U.S. Pat. No. 4,571,326 discloses a flat bed catalytic reactor system. U.S. Pat. No. 6,569,389 discloses a catalyst regenerator for removing hydrocarbon from deactivated catalyst withdrawn from a catalytic reactor.

There remains a continued need in the art for an integrated reactor and catalyst regeneration system that efficiently minimizes hydrocarbon accumulation. The presently disclosed subject matter provides such significant advantages over currently available systems.

SUMMARY

Disclosed herein are a catalyst reaction and regenerator system, a method of regenerating catalyst, and an apparatus for use in a catalyst reaction and regenerator system.

A catalyst reaction and regenerator system, comprises: a fluidized bed reactor comprising a catalyst riser having a partially perforated surface; and a reactor stripper in close proximity to the partially perforated surface of the catalyst riser; and a catalyst regenerator having at least two transfer lines to the fluidized bed reactor.

A method of regenerating catalyst, comprises: feeding a hydrocarbon mixture into a fluidized bed reactor, wherein the fluidized bed reactor comprises a catalyst riser having a partially perforated surface and a reactor stripper in close proximity to the partially perforated surface of the catalyst riser; generating a chemical product in the presence of a catalyst in the catalyst riser; separating the chemical product from the catalyst in the catalyst riser; feeding the catalyst from the catalyst riser to the reactor stripper; transferring the catalyst from the reactor stripper to a catalyst regenerator through a transfer line; and regenerating the catalyst in the catalyst regenerator, wherein the regenerated catalyst is transferred from the catalyst regenerator to the catalyst riser through a second transfer line.

An apparatus for use in a catalyst reaction and regenerator system comprises: a catalyst riser having a partially perforated surface; and a reactor stripper in close proximity to the partially perforated surface of the catalyst riser.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
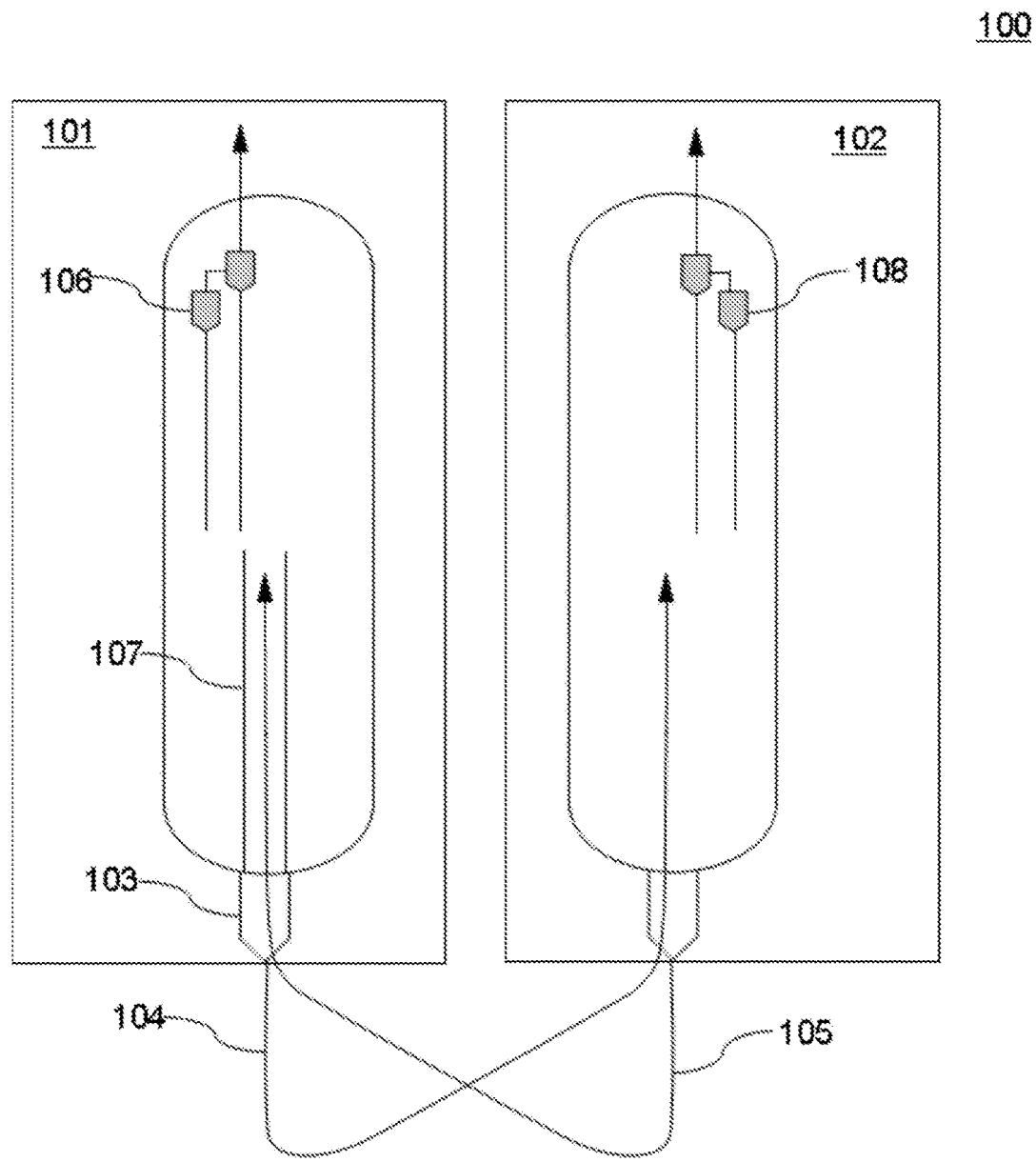
FIG. 1 depicts a system for regenerating catalyst according to one exemplary embodiment of the disclosed subject matter.

The presently disclosed subject matter relates to systems and processes for catalyst regeneration. In particular, the presently disclosed subject matter provides for an integrated fluidized bed reactor and catalyst regeneration system.

The presently disclosed subject matter relates to an integrated fluidized bed reactor and catalyst regeneration system. In particular, the presently disclosed subject matter provides for a catalyst riser of a fluidized bed reactor unit designed to minimize hydrocarbon accumulation.

In certain embodiments, the catalyst reactor and catalyst regeneration system of the presently disclosed subject matter includes (a) a fluidized bed reactor having a catalyst riser and a reactor stripper, and (b) a catalyst regenerator having at least two transfer lines to the fluidized bed reactor. In certain embodiments, one of the at least two transfer lines connects the catalyst riser to the catalyst regenerator. Alternatively or additionally, one of the at least two transfer lines connects the reactor stripper to the catalyst regenerator.

In certain embodiments, the catalyst riser has a partially perforated surface and the reactor stripper is placed in close proximity to the partially perforated surface of the catalyst riser. In certain embodiments, the perforated surface of the catalyst riser does not allow more than about 5% to about 10% of a catalyst to flow inside the catalyst riser from, the reactor stripper. The perforations of the catalyst riser minimize carbon accumulation on the surface on the catalyst riser and prevent drops in internal pressure and mandatory shutdowns.

In certain embodiments, the system of the presently disclosed subject matter further includes a second reactor unit. The system can include a third transfer line that connects the fluidized bed reactor to the second reactor. The third transfer line can be used to transfer the products generated from the fluidized bed reactor to the second reactor. For example, but not by way of limitation, the second reactor can be a methyl tert-butyl ether (MTBE) synthesis reactor.

The presently disclosed subject matter further provides for a method of regenerating catalyst. The method includes feeding a hydrocarbon mixture into a fluidized bed reactor, wherein the fluidized bed reactor includes a catalyst riser having a partially perforated surface and a reactor stripper in close proximity to the partially perforated surface of the catalyst riser. The method can further include generating a chemical product in the presence of a catalyst in the catalyst riser and separating the chemical product from the catalyst. The catalyst from the catalyst riser can be transferred to the reactor stripper. The method can further include transferring the catalyst from the reactor stripper to a catalyst regenerator through a transfer line. The method can further include regenerating the catalyst in the catalyst regenerator, wherein the regenerated catalyst is transferred from the catalyst regenerator to the fluidized bed reactor through a second transfer line.

In certain embodiments, the hydrocarbon mixture to be fed into the fluidized bed reactor includes iso-butane. In certain embodiments, dehydrogenation of iso-butane into iso-butylene, in the presence of a catalyst, is performed in the fluidized bed reactor. [0012] The method can further include transferring the separated chemical product from the fluidized bed reactor into a second reactor unit. The separated chemical product can be transferred to the second reactor to function as a feedstream for a second reaction. In certain embodiments, iso-butylene produced in the fluidized bed reactor can be transferred to a MTBE synthesis reactor as a feedstream for generating MTBE.

The term "about" or "approximately" means within an acceptable error range for the particular value as determined by one of ordinary skill in the art, which will depend in part on how the value is measure or determine, i.e., the limitations of the measurement system. For example, "about" can mean a range of up to 20%, up to 10%, up to 5%, and or up to 1% of a given value.

For the purpose of illustration and not limitation, FIG. 1 shows an integrated catalyst reaction and regenerator system in accordance with one embodiment of the disclosed subject matter. As shown in FIG. 1, system 100 includes a fluidized bed reactor 101 and a catalyst regenerator 102. The fluidized bed reactor 101 can further include a catalyst riser 107 and a reactor stripper 103. In certain embodiments, the surface of the catalyst riser 107 is partially perforated and the reactor stripper 103 is located in close proximity to the perforated surface of the catalyst riser.

The system 100 can further include at least two transfer lines 104,105. In certain embodiments, one of the two transfer lines 104 connects the reactor stripper 103 to the catalyst regenerator 102. The transfer line 104 connecting the reactor stripper 103 and the catalyst regenerator 102 can be disposed at various locations on the stripper and catalyst regenerator. For example, one end of the transfer line 104 can be located on the bottom of the reactor stripper 103 and the other end of the transfer line 104 can be located on the bottom of the catalyst regenerator 102. In certain embodiments, the transfer line 104 can connect the bottom of the reactor stripper 103 and the top of the catalyst regenerator 102. Additionally or alternatively, one of the two transfer lines 105 connects the catalyst regenerator 102 to the catalyst riser 107. The transfer line 105 connecting the catalyst riser 107 and the catalyst regenerator 102 can be disposed at various locations on the catalyst riser 107 and catalyst regenerator 102. For example, the transfer line 105 can connect the bottom of the catalyst riser 107 to the bottom of the catalyst regenerator 102.

The catalyst riser 107 of the fluidized bed reactor 101 can be at least partially perforated. For example, but not by way of limitation, about 0.5%, about 1%, about 5%, about 10%, about 15%, about 20%, about 25%, about 30%, about 40%, about 50%, about 60%, about 70%, about 80%, about 90% or about 100% of the total area of the catalyst riser is perforated. The perforations can be located at any position along the surface of the catalyst riser that is in close proximity to the reactor stripper. For example, the perforations can be located on the surface of the lower portion of the catalyst riser that is in close proximity to the reactor stripper.

In certain embodiments, catalyst that resides in the reactor stripper 103 can flow into the catalyst riser 107 through the perforations on the catalyst riser 107 surface. To minimize the amount of catalyst that can enter the catalyst riser, the size, shape and arrangement of the perforations can vary depending on the size and structure of the catalyst being used in the fluidized bed reactor 101. For example, but not by way of limitation, the perforations can be limited in size to not allow more than about 1%, more than about 2%, more than about 3%, more than about 4%, more than about 5%, more than about 6%, more than about 7%, more than about 8%, more than about 9% or more than about 10% of a catalyst to flow inside the catalyst riser from the reactor stripper. In certain embodiments, the perforations are limited in size to not allow more than about 5% to about 10% of the catalyst to flow inside the catalyst riser from the reactor stripper. In addition, the perforations can be of any shape including, but not limited to circular, rectangular, oval, star-shaped, triangle, square, octagon, hexagon, or combinations thereof. For example, the perforations can be circular in shape. The perforations of the partially perforated catalyst riser can be arranged in any manner, for example, the perforations can be arranged in parallel rows, in non-parallel rows, in branching patterns, in circular patterns, or combinations thereof.

The reactor stripper 103 of the fluidized bed reactor 101 can be located in close proximity to the partially perforated surface of the catalyst riser 107. In certain embodiments, the stripper at least partially overlaps the partially perforated surface of the catalyst riser. In certain embodiments, the perforated surface of the catalyst riser functions as the inner surface of the reactor stripper.

The reactor stripper 103 of the presently disclosed subject matter can be any stripper known to one of ordinary skill in the art. For example, but not by way of limitation, U.S. Pat. Nos. 6,248,298 and 7,744,746 and U.S. Patent Application No. 2011/0114468, incorporated herein by reference in their entireties, disclose strippers that can be used in the presently disclosed subject matter. The dimensions and structure of the reactor stripper of the presently disclosed subject matter can vary depending on the physical size of the reactor and the capacity of the reactor. The capacity of the integrated reactor system can be determined by the reaction rate and the stoichiometric quantities of the reactants. In certain embodiments, the reactor stripper can include a number of baffles, termed "sheds" from their shape in the form of inverted channel sections extending longitudinally in several superimposed rows or tiers across the body of the stripper. In certain embodiments, the reactor stripper includes one or more shed rows. For example, the reactor stripper can include seven (7) shed rows.

The fluidized bed reactor 101 can further include additional components and accessories including, but not limited to, one or more feed lines, gas exhaust lines, cyclones, product discharge lines, reaction zones and heating elements. The fluidized bed reactor can also include one or more measurement accessories. The one or more measurement accessories can be any suitable measurement accessory known to one of ordinary skill in the art including, but not limited to, pH meters, pressure indicators, pressure transmitters, thermowells, temperature-indicating controllers, gas detectors, analyzers and viscometers. The components and accessories can be placed at various locations on the fluidized bed reactor. In certain embodiments, the fluidized bed reactor can include one or more one feed lines, which can be disposed at any part of the reactor. For example, the feed line can be disposed at the bottom of the fluidized bed reactor. The fluidized bed reactor can further include one or more cyclones 106. The one or more cyclones can be used to separate the chemical product from the catalyst and to further remove the chemical product from the reactor through a product discharge line.

The catalyst regenerator 102 can also include additional components and accessories including, but not limited to, one or more gas inlet lines, flue gas exhaust lines, cyclones, reaction zones, heating elements, pH meters, pressure indicators, pressure transmitters, thermowells, temperature-indicating controllers, gas detectors, analyzers and viscometers. The components and accessories can be placed at various locations on the catalyst regenerator. In certain embodiments, the catalyst regenerator includes a gas inlet line to introduce regeneration gas into the catalyst regenerator, which can be disposed at any part of the reactor. For example, the gas inlet can be located at the bottom of the catalyst regenerator to fluidize the catalyst entering the regenerator from the reactor stripper. The catalyst regenerator can further include one or more cyclones 108 to separate the regeneration gas from the regenerated catalyst.

The catalyst riser of the presently disclosed subject matter is distinct from and has various advantages over the catalyst risers of fluid bed reactors known in the art. For example, the catalyst risers of fluid bed reactors known in the art have non-perforated surfaces. Additionally, the large differences in the temperatures of the reactor stripper and the catalyst riser results in condensation of hydrocarbons on the surface of the catalyst riser in the stripper section of fluidized bed reactors known in the art. This hydrocarbon buildup causes decreases in internal pressure resulting in mandatory shutdowns of the reactor and production loss. The addition of perforations on the surface of a catalyst riser within close proximity to the reactor stripper, in accordance with the subject matter of the present disclosure, minimizes the significant difference in temperature between the reactor stripper and the catalyst riser, thereby reducing the hydrocarbon buildup on the surface of the catalyst riser and the loss in productivity.

A catalyst riser according to the presently disclosed subject matter can be used in any fluidized bed reactor and regenerator system known to one of ordinary skill in the art. For example, any fluidized bed reactor and regenerator system that utilizes a catalyst riser and a stripper located in close proximity to the catalyst riser can use the catalyst riser of the presently disclosed subject matter. A non-limiting example of a fluidized bed reactor and regenerator system that can use the catalyst riser of the presently disclosed subject matter is disclosed in U.S. Pat. No. 6,248,298, which is incorporated herein by reference in its entirety. An additional non-limiting example of a fluidized bed reactor/regenerator system includes the SADAF FBD-4 reactor/regeneration system.

In certain embodiments, the system of the presently disclosed subject matter can include a second reactor unit. The system can further include a third transfer line that connects the fluidized bed reactor to the second reactor. The second reactor unit can be any reactor known to one of ordinary skill in the art. For example, the second reactor unit can be a reactor that uses the chemical products generated in the fluidized bed reactor as reactants. Non-limiting examples of second reactor include, but are not limited to, reactors that are used to generate acrylates, methylacrylates, polybutene, methyl tert-butyl ether (MTBE) or butyl rubber. In certain embodiments, the second reactor can be a MTBE synthesis reactor.

In accordance with the embodiments of the subject matter previously described, the fluidized bed reactor, catalyst regenerator, catalyst riser, reactor striper, second reactor and the various components and accessories that can be included in the fluidized bed reactor and catalyst regenerator can be made out of a plurality of suitable materials. Suitable materials include, but are not limited to, stainless steel, carbon steel, glass-lined materials, polymer-based materials, nickel-base metal alloys, cobalt-based metal alloys or combinations thereof.

Figure 2:
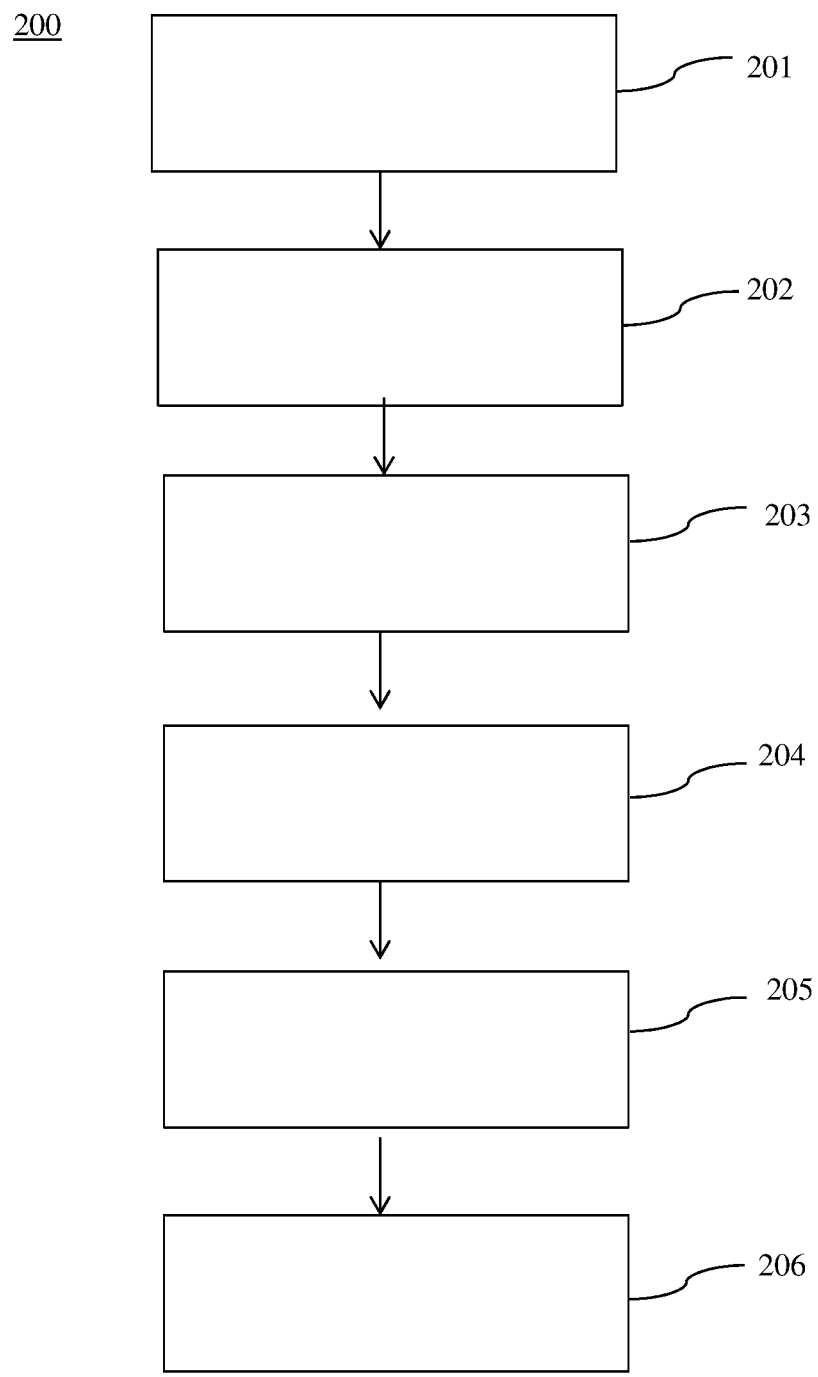
FIG. 2 depicts a method for regenerating catalyst according to one exemplary embodiment of the disclosed subject matter.

The presently disclosed subject matter further provides for a method of regenerating catalyst. For the purpose of illustration and not limitation, FIG. 2 shows a method 200 for regenerating catalyst in accordance with one embodiment of the disclosed subject matter. As shown in FIG. 2, the method of regenerating catalyst 200 includes providing a feedstream of a hydrocarbon mixture into the fluidized bed reactor 201, wherein the fluidized bed reactor includes a catalyst riser having a partially perforated surface and a reactor stripper in close proximity to the partially perforated surface.

The method 200 can further include generating a chemical product in the presence of a catalyst 202. Within the catalyst riser of the fluidized bed reactor, the catalyst contacts the hydrocarbon mixture feedstream and catalyzes a chemical reaction to form a chemical product. Non-limiting examples of chemical reactions that can occur in the catalyst riser of the present disclosure include, but are not limited to, dehydrogenation and dehydration reactions. Additional non-limiting examples of chemical reactions that can occur in the catalyst riser of the present disclosure include dehydrogenation of iso-butane to iso-butylene, dehydrogenation of cyclohexane to benzene, dehydration of glycerol to acrolein, dehydration of the lactic acid to acrylic acid, dehydration of 3-hydroxypropionic acid to acrylic acid, dehydration of 3-hydroxyisobutyric acid methacrylic acid or dehydration of the 2-hydroxyisobutyric acid. In certain embodiments, the hydrocarbon mixture includes iso-butane. In certain embodiments, the hydrocarbon mixture can further include oxygen. In certain embodiments, iso-butane contained within the hydrocarbon mixture can undergo dehydrogenation, in the presence of a catalyst, to form iso-butylene as a chemical product.

The catalysts to be used and regenerated in the method and system of the disclosed subject matter can be any catalyst known to one of ordinary skill in the art. For example, U.S. Pat. Nos. 4,766,266, 4,727,216 and 5,593,935, incorporated herein by reference in their entireties, disclose catalysts that can be used and regenerated in the disclosed method and system. Additional non-limiting examples of catalysts include catalysts that are platinum-based or chromium (III) oxide-based.

The method 200 can further include separating the catalyst from the chemical product 203 and feeding the catalyst from the catalyst riser to the reactor stripper 204. The catalyst can be separated from the chemical product and transferred to the reactor stripper by any method known to one of ordinary skill in the art. In certain embodiments, catalyst from the catalyst riser can be separated from the chemical product by one or more cyclones and can flow downwardly within the fluidized bed reactor by means of gravity into the upper portion of the stripper. Catalyst in the fluidized bed reactor is gradually deactivated primarily due to the accumulation of hydrocarbon, i.e., coke, on the surface and within the pores of the catalyst. To maintain catalyst activity, the reactor stripper functions to at least partially remove the hydrocarbon material that is associated with the deactivated catalyst prior to entry into the catalyst regenerator. Hydrocarbon on the surface and within the pores of the deactivated catalyst can be removed within the reactor stripper by contact with a stripping gas. Non-limiting examples of a stripping gas include nitrogen, $CO_2$, water vapor, recycle gas, obtained as exhaust from the chemical reaction, or combinations thereof. Catalyst residence time in the stripper can be from about 30 seconds to about 5 minutes. In certain embodiments, the catalyst residence time is from about 1 to about 2 minutes.

In certain embodiments, the reactor stripper is located in close proximity to the partially perforated surface of the catalyst riser. The internal pressure differences between the catalyst riser and the stripper can result in catalyst residing in the reactor stripper to flow into the catalyst riser through the perforations on the surface of the catalyst riser. In certain embodiments, the method can include the flow of less than about 0.5%, about 1%, about 2%, about 3%, about 4%, about 5%, about 6%, about 7%, about 8%, about 9% or about 10% of catalyst from the reactor stripper into the catalyst riser. In certain embodiments, the method can include the flow of less than about 0.5% to about 10% of catalyst from the reactor stripper into the catalyst riser.

The method 200 can further include transferring the catalyst from the reactor stripper to the catalyst regenerator 205 through a transfer line. After the deactivated catalyst is at least partially stripped of hydrocarbon that has accumulated on its surface and within its pores, the deactivated catalyst can be transferred to the catalyst regenerator for further hydrocarbon removal. In certain embodiments, the catalyst can be moved within the transfer line by contact with a carrier gas. The carrier gas can include, but is not limited to, air, oxygen-rich gas, oxygen-lean gas, ozone, carbon monoxide, carbon dioxide, nitrogen, combustion gas, exhaust gas or combinations thereof. In certain embodiments, the carrier gas includes air. In certain embodiments, the slope and/or decline of the transfer line can assist in moving the catalyst through the transfer line to the catalyst regenerator.

The method 200 can further include regenerating the deactivated catalyst in the catalyst regenerator 206. In the catalyst regenerator, the deactivated catalyst can be subjected to regeneration gas at temperatures from about 590° C. to about 760° C. to remove the residual hydrocarbon and coke deposits from the catalyst prior to sending the catalyst, in its regenerated state, back to the fluidized bed reactor. In certain embodiments, the hydrocarbon deposits on the deactivated catalyst are oxidized in the presence of regeneration gas to form a regenerated catalyst and a regenerator flue gas. The regeneration gas can be introduced in an amount sufficient for fluidizing the catalyst, and the regeneration gas can include air, optionally preheated air, oxygen supplemented air or combinations thereof. The regenerated catalyst can be separated from the regeneration gas and flue gas by a cyclone separator. The separated regenerated catalyst can be transferred to the fluidized bed reactor to continue catalyzing the reaction. The duration of the regeneration process can vary widely and is dependent on the degree of decoking that is desired. For example, the time during which the deactivated catalyst is exposed to the regeneration gas can be from about 0.5 to about 10 hours.

After regeneration, the regenerated catalyst can be transferred to the fluidized bed reactor 206 through a transfer line. In certain embodiments, the regenerated catalyst can be transferred directly to the catalyst riser to displace the deactivated catalyst and ensure continuous production of chemical products. In certain embodiments, the regenerated catalyst can be moved within the transfer line by contact with a carrier gas. The carrier gas can include, but is not limited to, natural gas, air, oxygen-rich gas, oxygen-lean gas, ozone, carbon monoxide, carbon dioxide, nitrogen, steam combustion or exhaust gas, or any combination thereof. In certain embodiments, the carrier gas includes natural gas.

In certain embodiments of the present disclosure, the method of regenerating catalyst can further include feeding the separated chemical product from the fluidized bed reactor to a second reactor through a transfer line. For example, the product generated in the fluidized bed reactor can be separated from the catalyst by passing through a cyclone. The cyclone can be coupled to a transfer line to transport the chemical product from the fluidized bed reactor to a second reactor. In certain embodiments, the chemical product generated in the fluidized bed reactor includes iso-butylene, which can be transferred to a second reactor as a feedstream to generate a chemical product including, but not limited to, polybutene, butyl rubber, methyl acrylate and MTBE in the second reactor. For example, the second reactor can be a MTBE synthesis reactor for producing MTBE from iso-butylene.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The systems, apparatus, and methods of making disclosed herein include(s) at least the following embodiments:

Embodiment 1

A catalyst reaction and regenerator system, comprising: a fluidized bed reactor comprising: a catalyst riser having a partially perforated surface; and a reactor stripper in close proximity to the partially perforated surface of the catalyst riser; and a catalyst regenerator having at least two transfer lines to the fluidized bed reactor.

Embodiment 2

The system of Embodiment 1, wherein one of the transfer lines connects the catalyst riser to the catalyst regenerator.

Embodiment 3

The system of Embodiment 1 or Embodiment 2, wherein one of the two transfer lines connects the reactor stripper and the catalyst regenerator.

Embodiment 4

The system of any of Embodiments 1-3, wherein the perforated surface of the catalyst riser does not allow more than about 5% to about 10% of a catalyst to flow inside the catalyst riser from the reactor stripper.

Embodiment 5

The system of any of Embodiments 1-4, wherein the partially perforated surface of the catalyst riser minimizes coke formation.

Embodiment 6

The system of any of Embodiments 1-5, wherein the system further comprises a second reactor.

Embodiment 7

The system of Embodiment 6, wherein the second reactor is connected to the fluidized bed reactor by a transfer line.

Embodiment 8

A method of regenerating catalyst, comprising: feeding a hydrocarbon mixture into a fluidized bed reactor, wherein the fluidized bed reactor comprises a catalyst riser having a partially perforated surface and a reactor stripper in close proximity to the partially perforated surface of the catalyst riser; generating a chemical product in the presence of a catalyst in the catalyst riser; separating the chemical product from the catalyst in the catalyst riser; feeding the catalyst from the catalyst riser to the reactor stripper; transferring the catalyst from the reactor stripper to a catalyst regenerator through a transfer line; and regenerating the catalyst in the catalyst regenerator, wherein the regenerated catalyst is transferred from the catalyst regenerator to the catalyst riser through a second transfer line.

Embodiment 9

The method of Embodiment 8, wherein the perforated surface of the catalyst riser allows less than about 5% to about 10% of the catalyst to flow inside the catalyst riser from the reactor stripper.

Embodiment 10

The method of Embodiment 8 or Embodiment 9, wherein the method minimizes coke formation on a surface of the catalyst riser.

Embodiment 11

The method of any of Embodiments 8-10, wherein the hydrocarbon mixture comprises iso-butane.

Embodiment 12

The method of any of Embodiments 8-11, wherein the chemical product comprises iso-butylene.

Embodiment 13

An apparatus for use in a catalyst reaction and regenerator system comprising: a catalyst riser having a partially perforated surface; and a reactor stripper in close proximity to the partially perforated surface of the catalyst riser.

Embodiment 14

The apparatus of Embodiment 13, wherein the perforated surface of the catalyst riser allows less than about 5% to about 10% of a catalyst to flow inside the catalyst riser from the reactor stripper.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

While the disclosed subject matter is described herein in terms of certain embodiments and representative examples, those skilled in the art will recognize that various modifications and improvements can be made to the disclosed subject matter without departing from the scope thereof. Additional features known in the art likewise can be incorporated. Moreover, although individual features of one embodiment of the disclosed subject matter can be discussed herein and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compositions and methods of the disclosed subject matter without departing from the spirit or scope of the disclosed subject matter. Thus, it is intended that the disclosed subject matter include modifications and variations that are within the scope of the appended claims and their equivalents.

Various publications, patents and patent applications are cited herein, the contents of which are hereby incorporated by reference in their entireties.

The invention claimed is:

1. A method of regenerating catalyst, comprising:
feeding a hydrocarbon mixture into a fluidized bed reactor, wherein the fluidized bed reactor comprises a catalyst riser having a partially perforated surface and a reactor stripper in close proximity to the partially perforated surface of the catalyst riser;
generating a chemical product in the presence of a catalyst in the catalyst riser;
separating the chemical product from the catalyst in the catalyst riser;
feeding the catalyst from the catalyst riser to the reactor stripper;
transferring the catalyst from the reactor stripper to a catalyst regenerator through a transfer line; and
regenerating the catalyst in the catalyst regenerator, wherein the regenerated catalyst is transferred from the catalyst regenerator to the catalyst riser through a second transfer line,
wherein
the method minimizes coke formation on a surface of the catalyst riser,
the hydrocarbon mixture comprises iso-butane, or
the chemical product comprises iso-butylene.

2. The method of claim 1, wherein the method minimizes coke formation on a surface of the catalyst riser.

3. The method of claim 1, wherein the hydrocarbon mixture comprises iso-butane.

4. The method of claim 1, wherein the chemical product comprises iso-butylene.

5. A method of regenerating catalyst, comprising:
feeding a hydrocarbon mixture into a fluidized bed reactor, wherein the fluidized bed reactor comprises a catalyst riser having a partially perforated surface and a reactor stripper in close proximity to the partially perforated surface of the catalyst riser;
generating a chemical product in the presence of a catalyst in the catalyst riser;
separating the chemical product from the catalyst in the catalyst riser;
feeding the catalyst from the catalyst riser to the reactor stripper;
transferring the catalyst from the reactor stripper to a catalyst regenerator through a transfer line; and
regenerating the catalyst in the catalyst regenerator, wherein the regenerated catalyst is transferred from the catalyst regenerator to the catalyst riser through a second transfer line, wherein the perforated surface of the catalyst riser allows less than about 5% to about 10% of the catalyst to flow inside the catalyst riser from the reactor stripper.

6. The method of claim 5, wherein the method minimizes coke formation on a surface of the catalyst riser.

7. The method of claim 5, wherein the hydrocarbon mixture comprises iso-butane.

8. The method of claim 5, wherein the chemical product comprises iso-butylene.

* * * * *